(12) United States Patent
Johal et al.

(10) Patent No.: US 6,455,297 B1
(45) Date of Patent: Sep. 24, 2002

(54) METHODS AND COMPOSITIONS FOR REGULATING CELL DEATH AND ENHANCING DISEASE RESISTANCE TO PLANT PATHOGENS

(75) Inventors: Gurmukh S. Johal, Johnston, IA (US); Steven P. Briggs, Del Mar, CA (US); John Gray, Toledo, OH (US); Gongshe Hu, Albany, CA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/923,654

(22) Filed: Aug. 7, 2001

Related U.S. Application Data

(60) Continuation of application No. 09/798,373, filed on Mar. 2, 2001, which is a division of application No. 09/260,843, filed on Mar. 2, 1999, now Pat. No. 6,271,439.
(60) Provisional application No. 60/076,754, filed on Mar. 4, 1998.

(51) Int. Cl.[7] .............................. C12N 9/88; C12N 1/20; C12N 15/00; C12P 21/06; C07H 21/04

(52) U.S. Cl. .................. 435/232; 435/69.1; 435/252.3; 435/320.1; 536/23.1; 536/23.2; 530/300; 530/350; 530/376

(58) Field of Search .............................. 435/232, 252.3, 435/320.1, 69.1; 536/23.1, 23.2; 530/300, 350, 376

(56) References Cited

U.S. PATENT DOCUMENTS 5,939,602 A    8/1999    Volrath et al. .............. 800/300

FOREIGN PATENT DOCUMENTS

| DE | 19621572 A1 | 5/1996 |
| DE | 19621572 | 12/1997 |
| WO | WO 94/16077 A1 | 7/1994 |
| WO | WO 95/31564 A2 | 11/1995 |
| WO | WO 96/22016 A1 | 7/1996 |
| WO | WO 96/28561 A1 | 9/1996 |
| WO | WO 96/31597 A1 | 10/1996 |
| WO | WO 96/36697 A1 | 11/1996 |
| WO | WO 98/04586 A2 | 2/1998 |

OTHER PUBLICATIONS

Mock et al. [Plant Mol. Bill. 28 : 245–256, 1995].*
Dangl et al., Death Don't Have No Mercey: Cell Death Programs in Plant–Microbe Interactions, The Plant Cell, Oct. 1996, pp. 1793–1807, vol. 8, American Society of Plant Physiologists.
GenBank Report, Accession No. X82832, Mock et al., "Isolation, Sequencing, and Expression of cDNA Sequences Encoding Uroporphyrinogen Decarboxylase from Tobacco and Barley," Plant Molecular Biology, 1995, pp. 245–256, vol. 28 (2); Mock, H., Direct Submission, Submitted Nov. 21, 1994.
GenBank Report, Accession No. X82833, Mock et al., "Isolation, Sequencing, and Expression of cDNA Sequences Encoding Uroporphyrinogen Decarboxylase from Tobacco and Barley," Plant Molecular Biology, 1995, pp. 245–256, vol. 28 (2); Mock, H. Direct Submission, Submitted Nov. 21, 1994.
GenBank Report, Accession No. NM 000374, Romeo et al., "Molecular Cloning and Nucleotide Sequence of a Complete Human Uroporphyrinogen Decarboxylase cDNA," Journal of Biological Chemistry, 1986, pp. 9825–9831, vol. 261 (21).
Hu et al., Isolation and Characterization of Les–2552, a Dominant Lesion–Mimic Mutation in Maize, Plant Physiology Supplement, Poster Presented, Jul. 1997, p. 187, vol. 114, No. 3.
Hu et al., A Porphyrin Pathway Impairment is Responsible for the Phenotype of a Dominant Disease Lesion Mimic Mutant of Maize, The Plant Cell, Jul. 1998, pp. 1095–1105, vol. 10, American Society of Plant Physiologists.
Johal et al. "Cell Death Mechanisms During the Expression of Two Lesion Mimic Mutations of Maize," Plant Physiology Supplement, 1997, 114(3):10, The Quadrennial Joint Annual Meetings of Plant Physiologists and the Canadian Society of Plant Physiologists.
Johal et al., A Tale of Two Mimics; Transposon Mutagenesis and Characterization of Two Disease Lesion Mimic Mutations of Maize, XP002068008, 1994, pp. 69–76, vol. 39, Maydica.
Johal, et al., Disease Lesion Mimics of Maize: A Model for Cell Death in Plants, Bioessays, 1995, pp. 685–692, vol. 17, No. 8.

(List continued on next page.)

Primary Examiner—Tekchand Saidha
(74) Attorney, Agent, or Firm—Alston & Bird LLP

(57) ABSTRACT

Compositions and methods for enhancing disease resistance to a pathogen in a plant are provided. Methods of the invention comprise stably transforming a plant with an antisense nucleotide sequence for a gene encoding an enzyme in the C-5 porphyrin metabolic pathway and operably linking said antisense sequence to a pathogen-inducible promoter, such that invasion of a cell by a pathogen elicits a hypersensitive-like response that results in confinement of the pathogen to cells of initial contact. Transformed plants and seeds are provided. Nucleotide sequences encoding a wild-type maize urod gene useful in the present invention and the amino acid sequence for the protein encoded thereby are provided. These compositions are also useful for regulating cell death in specifically targeted tissues. A maize lesion mimic, dominant mutant phenotype, designated Les22, and the molecular basis for its manifestation are also provided.

6 Claims, 2 Drawing Sheets

OTHER PUBLICATIONS

Mock et al., Isolation, Sequencing and Expression of cDNA Sequences Encoding Unroporphyrinogen Decarboxylase From Tobacco and Barley, Plant Molecular Biology, 1995, pp. 245–256, vol. 28, Klawer Academic Publishers, Belgium.

Mock et al., Reduction of Uroporphyrinogen Decarboxylase by Antisense RNA Expression Affects Activities of Other Enzymes Involved in Tetrapyrrole Biosynthesis and Leads to Light–Dependent Necrosis, Plant Physiology, Apr. 1997, pp. 1101–1112, vol. 113.

Mock et al., Defense Responses to Tetrapyrrole–Induced Oxidative Stress in Transgenic Plants with Reduced Uroporphyrinogen Decarboxylase or Coproporinogen Oxidase Activity, Plant Physiol., 1998, pp. 107–116, vol. 116.

Mock et al., Expression of Uroporphyrinogen Decarboxylase or Coproporphyrinogen Oxidase Antisense RNA in Tobacco Induces Pathogen Defense Responses Conferring Increased Resistance to Tobacco Mosaic Virus, The Journal of Biological Chemistry, Feb. 1999, pp. 4231–4238, vol. 274, No. 7, The American Society of Biochemistry and Molecular Biology.

Mock et al., "Reduction of Uroporphyrinogen Decarboxylase by Antisense RNA Expression Affects Activities of Other Enzymes Involved in Tetrapyrrole Biosynthesis and Leads to Light–Dependent Necrosis," *Plant Physiology,* 1997, pp. 1101–1112, vol. 113, American Society of Plant Physiologists, USA.

Reinbothe et al., "Regulation of Chlorophyll Biosynthesis in Angiosperms," *Plant Physiology,* 1996, pp. 1–7, vol. 111, American Society of Plant Physiologists, USA.

Shah et al., Resistance to Disease and Insectws to Transgenic Plants: Progress and Applications to Agriculture, Trends in Biotechnology, pp. 362–368, vol. 13, No. 9, Elsevier Science Ltd.

Shalygo, N.V., Prophyrin Precursors of Chlorophyll: Identification and Characteristics of Their Physiological Activity in Green Barley Seedlings, *Russian Journal of Plant Physiology,* 1999, pp. 598–603, vol. 46, No. 5, Translated from Fiziologlya Rastenll, 1999, pp. 686–692, vol. 46, No. 5, Original Russian Text.

\* cited by examiner

METHODS AND COMPOSITIONS FOR REGULATING CELL DEATH AND ENHANCING DISEASE RESISTANCE TO PLANT PATHOGENS

CROSS-REFERENCE TO RELATED APPLICATION

This application is a continuation of U.S. application Ser. No. 09/798,373, filed Mar. 2, 2001, which is a division of U.S. application Ser. No. 09/260,843, filed Mar. 2, 1999, which claims the benefit of U.S. Provisional Application Serial No. 60/076,754, filed Mar. 4, 1998, the disclosures of which are herein incorporated by reference.

FIELD OF THE INVENTION

The invention relates to the genetic manipulation of plants, particularly to transforming plants with nucleotide sequences that regulate cell death and enhance disease resistance.

BACKGROUND OF THE INVENTION

A host of cellular processes enable plants to defend themselves from disease caused by pathogenic agents. These processes apparently form an integrated set of resistance mechanisms that is activated by initial infection and then limits further spread of the invading pathogenic microorganism.

Subsequent to recognition of a potentially pathogenic microbe, plants can activate an array of biochemical responses. Generally, the plant responds by inducing several local responses in the cells immediately surrounding the infection site. The most common resistance response observed in both nonhost and race-specific interactions is termed the "hypersensitive response" (HR). In the hypersensitive response, cells contacted by the pathogen, and often immediately adjacent cells, rapidly collapse and dry in a necrotic fleck. Other responses include the deposition of callose, the physical thickening of cell walls by lignification, and the synthesis of various antibiotic small molecules and proteins. Genetic factors in both the host and the pathogen determine the specificity of these local responses, which can be very effective in limiting the spread of infection to localized lesions.

The hypersensitive response in many plant-pathogen interactions results from the expression of a resistance (R) gene in the plant and a corresponding avirulence (avr) gene in the pathogen. The resistance gene in the plant and the avirulence gene in the pathogen often conform to a gene-for-gene relationship. That is, resistance to a pathogen is only observed when the pathogen carries a specific avirulence gene and the plant carries a corresponding or complementing resistance gene. Hence, there is a specificity requirement to bring about enhanced disease resistance using the avr::R gene-for-gene hypersensitive response.

Many environmental and genetic factors cause general leaf necrosis in maize and other plants. In addition, numerous recessive and dominant genes cause the formation of discrete or expanding necrotic lesions of varying size, shape, and color (see, for example, Wolter et al. (1993) *Mol. Gen. Genet.* 239:122; Dietrich et al. (1994) *Cell* 77:565; Greenberg et al. (1994) *Cell* 77:551). Because lesions of some of these mutants resemble those associated with known diseases of maize, these genetic defects have been collectively called disease lesion mimics.

Lesion mimic mutations of maize have been shown to be specified by more than forty independent loci. It is intriguing that more than two thirds of these disease lesion mimic mutations display a partially dominant, gain-of-function inheritance, making it the largest class of dominant mutants in maize. These lesion mimic plants produce discrete disease-like symptoms in the absence of any invading pathogens.

Despite the availability of the large number of lesion mimic mutations in plants, the mechanistic basis and significance of this phenomenon, and the wild-type function of the genes involved, are poorly understood. The expression of most, if not all, lesion mimics is developmentally programmed and is easily affected by genetic background. One nearly ubiquitous feature of most mimics is the death of afflicted tissues, the extent of which is often enhanced by intense light, making it likely that reactive oxygen species are involved in the etiology of lesion mimics (see, for example, Johal et al. (1995) *BioEssays* 17:685; Dangl et al. (1996) *Plant Cell* 8:1793). In fact, superoxide has been shown to be responsible for the expression of lesions in the Arabidopsis lsd1 mutant (Jabs et al. (1996) *Science* 273:1853). The existence of both determinant and propagative lesion type mimics suggests that cell death is either initiated precociously or is contained inadequately in these mutants. Since cell death in plants, like in animals, has relevance to development, differentiation, and maintenance, lesion mimics afford an excellent model for understanding how cell death is regulated and executed in plants. Recently, genes for three mimics from three plant species have been cloned (Buschges et al. (1997) *Cell* 88:695–705; Dietrich et al. (1997) *Cell* 88:685–694; Gray et al. (1997) *Cell* 89:25–31). As expected from their recessive loss-of-function phenotypes, they all appear to encode cell death suppressible functions that are unique to plants.

While it is relatively straightforward to comprehend the nature of the defect in a recessive loss-of-function mutation, it is often not possible to predict from the phenotype what the mechanistic basis of a dominant mutation might be. One such maize dominant mutation is Les22 (previously designated Les*–2552), which is characterized by the formation of discrete, tiny whitish gray bleached or necrotic spots on leaf blades that partly resemble hypersensitive response lesions in appearance. Like most lesion mimics of maize, the expression of Les22 lesions is cell autonomous, developmentally dictated, and light-dependent.

Cell death and lesion formation during the expression of disease mutant mimics is frequently mediated by oxygen free radicals, which also mediate cell death and lesion formation during the hypersensitive response associated with gene-for-gene specificity of plant-pathogen interactions. The molecular basis for this similarity can be used to genetically engineer plants for enhanced disease resistance.

SUMMARY OF THE INVENTION

Compositions and methods for creating or enhancing disease resistance to a pathogen in a plant are provided. The methods comprise genetically engineering a plant to initiate a nonspecific hypersensitive-like response upon pathogenic invasion of a plant cell. More particularly, the invention discloses methods for stably transforming a plant with an antisense nucleotide sequence for a gene involved in regulation of the C-5 porphyrin metabolic pathway. The antisense sequence is operably linked to a pathogen-inducible promoter. Expression of the antisense nucleotide sequence in response to pathogenic invasion of a cell effectively disrupts porphyrin metabolism of the transformed plant cell of the present invention. As a result, photosensitive porphyrins accumulate, leading to a hypersensitive-like response within the invaded cell and development of a localized lesion wherein the spread of the pathogen is contained.

Transformed plants and seeds, as well as methods for making such plants and seeds are additionally provided.

Nucleotide sequences encoding a wild-type maize urod gene useful in the present invention and the amino acid sequence for the protein encoded thereby are provided. These compositions are also useful for regulating cell death in specifically targeted tissues.

A maize lesion mimic, dominant mutant phenotype, designated Les22, and the molecular basis for its manifestation are also provided.

DETAILED DESCRIPTION OF THE INVENTION

Figure 1:
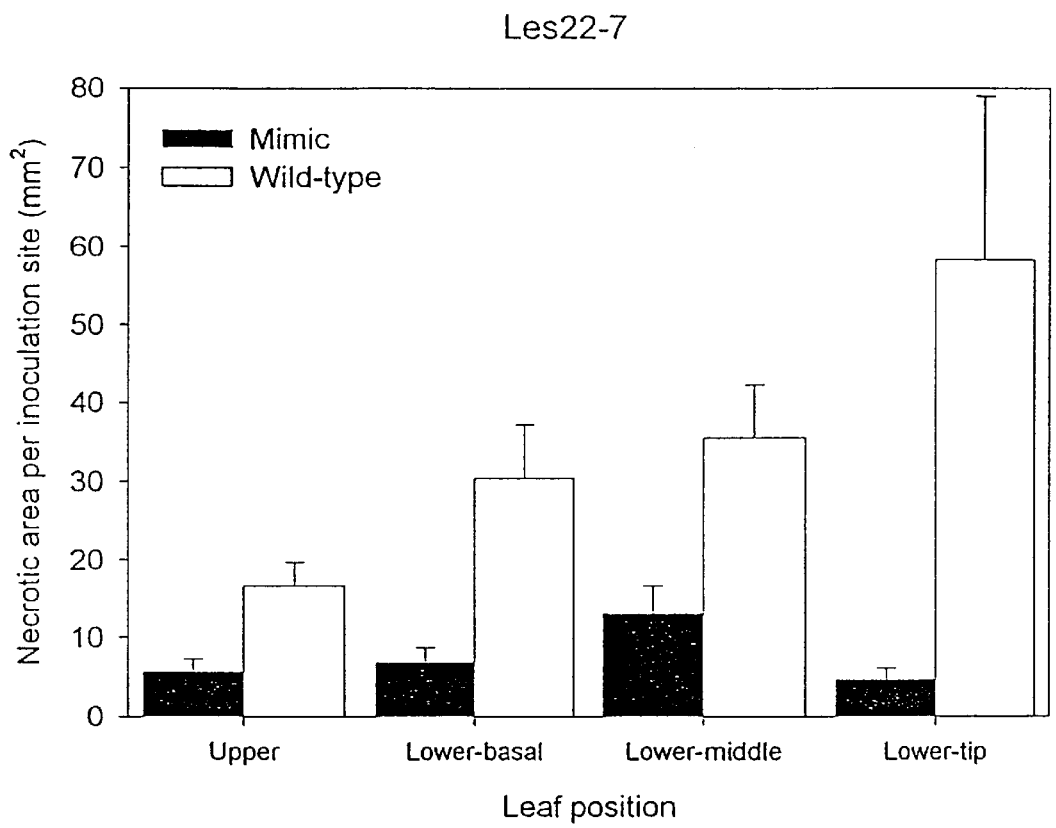
FIG. 1 shows the area of pathogen-associated necrotic tissue on lesion-expressing leaves, as well as those that at the time of inoculation were free of Les22 lesions, and corresponding tissue of wild-type sibs ten days following inoculation of leaf tissue with *C. heterostrophus* (Drechs.) spores. Results shown represent the mean ±SEM for two inoculations per tissue type per plant for a total of four plants per genotype.

The present invention is drawn to compositions and methods for creating or enhancing disease resistance in a plant. Accordingly, the methods are also useful in protecting plants against pathogens. By "disease resistance" is intended that the plants avoid the disease symptoms that are the outcome of plant-pathogen interactions. That is, pathogens are prevented from causing plant diseases and the associated disease symptoms. The methods of the invention can be utilized to protect plants from disease, particularly those diseases that are caused by plant pathogens.

Pathogens of the invention include, but are not limited to, viruses or viroids, bacteria, insects, fungi, and the like. Viruses include tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthephaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassuicola, Septoria glycines, Phyllosticta sojicola, Alternaria alternata, Pseudomonas syringae* p.v. *glycinea, Xanthomonas campestris* p.v. *phaseoli, Microsphaera diffuse, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines* Fusarium solani; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganese* subsp. *insidiosum, Pythium ultimum, Pythium irregulars, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis,* Fusarium, *Xanthomonas campestris* p.v. *alfalfae, Aphanomyces euteiches, Stemphylium herbarum, Stemphylium alfalfae;* Wheat: *Pseudomonas syringae* p.v. *atrofaciens, Urocystis agropyri, Xanthomonas campestris*p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora triticirepentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis;* Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi,*

*Ascochyta sorghina, Pseudomonas syringae* p.v. *syringae, Xanthomonas campestris* p.v. *holcicola, Pseudomonas andropogonis, Pucciniapurpurea, Macrophominaphaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root knot, cyst and lesion nematodes, etc.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; Diatraea saccharalis, sugarcane borer; *Diabrotica virgifera,* western corn rootworm; *Diabrotica longicornis barberi,* northern corn rootworm; *Diabrotica undecimpunctata howardi,* southern corn rootworm; Melanotus spp., wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafininer; *Anaphothrips obscrurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; Eleodes, Conoderus, and Aeolus spp., wireworms; *Oulema melanopus,* cereal leaf beetle; *Chaetocnema pulicaria,* corn flea beetle; *Sphenophorus maidis,* maize billbug; *Rhopalosiphum maidis;* corn leaf aphid; *Sipha flava,* yellow sugarcane aphid; *Blissus leucopterus leucopterus,* chinch bug; *Contarinia sorghicola,* sorghum midge; *Tetranychus cinnabarinus,* carmine spider mite; *Tetranychus urticae,* twospotted spider mite; Wheat: *Pseudaletia unipunctata,* army worm; *Spodoptera frugiperda,* fall armyworm; *Elasmopalpus lignosellus,* lesser cornstalk borer; *Agrotis orthogonia,* western cutworm; *Elasmopalpus lignosellus,* lesser cornstalk borer; *Oulema melanopus,* cereal leaf beetle; *Hypera punctata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femurrubrum,* redlegged grasshopper; *Melanoplus differentialis,* differential grasshopper; *Melanoplus sanguinipes,* migratory grasshopper; *Mayetiola destructor,* Hessian fly; *Sitodiplosis mosellana,* wheat midge; *Meromyza americana,* wheat stem maggot; *Hylemya coarctata,* wheat bulb fly; *Frankliniella fusca,* tobacco thrips; *Cephus cinctus,* wheat stem sawfly; *Aceria tulipae,* wheat curl mite; Sunflower: *Suleima helianthana,* sunflower bud moth; *Homoeosoma electellum,* sunflower moth; *zygogramma exclamationis,* sunflower beetle; *Bothyrus gibbosus,* carrot beetle; *Neolasioptera murtfeldtiana,* sunflower seed midge; Cotton: *Heliothis virescens,* cotton budworm; *Helicoverpa zea,* cotton bollworm; *Spodoptera exigua,* beet armyworm; *Pectinophora gossypiella,* pink bollworm; *Anthonomus grandis,* boll weevil; *Aphis gossypii,* cotton aphid; *Pseudatomoscelis seriatus,* cotton fleahopper; *Trialeurodes abutilonea,* bandedwinged whitefly; *Lygus lineolaris,* tarnished plant bug; *Melanoplus femurrubrum,* redlegged grasshopper; *Melanoplus differentialis,* differential grasshopper; *Thrips tabaci,* onion thrips; *Franklinkiella fusca,* tobacco thrips; *Tetranychus cinnabarinus,* carmine spider mite; *Tetranychus urticae,* twospotted spider mite; Rice: *Diatraea saccharalis,* sugarcane borer; *Spodoptera frugiperda,* fall armyworm; *Helicoverpa zea,* corn earworm; *Colaspis brunnea,* grape colaspis; *Lissorhoptrus oryzophilus,* rice water weevil; *Sitophilus oryzae,* rice weevil; *Nephotettix nigropictus,* rice leafhopper; *Blissus leucopterus leucopterus,* chinch bug; *Acrosternum hilare,* green stink bug; Soybean: *Pseudoplusia includens,* soybean looper; *Anticarsia gemmatalis,* velvetbean caterpillar; *Plathypena scabra,* green cloverworm; *Ostrinia nubilalis,* European corn borer; *Agrotis ipsilon,* black cutworm; *Spodoptera exigua,* beet armyworm; *Heliothis virescens,* cotton budworm; *Helicoverpa zea,* cotton bollworm; *Epilachna varivestis,* Mexican bean beetle; *Myzus persicae,* green peach aphid; *Empoasca fabae,* potato leafhopper; *Acrosternum hilare,* green stink bug; *Melanoplus femurrubrum,* redlegged grasshopper; *Melanoplus differentialis,* differential grasshopper; *Hylemya platura,* seedcorn maggot; *Sericothrips variabilis,* soybean thrips; *Thrips tabaci,* onion thrips; *Tetranychus turkestani,* strawberry spider mite; *Tetranychus urticae,* twospotted spider mite; Barley: *Ostrinia nubilalis,* European corn borer; *Agrotis ipsilon,* black cutworm; *Schizaphis graminum,* greenbug; *Blissus leucopterus leucopterus,* chinch bug; *Acrosternum hilare,* green stink bug; *Euschistus servus,* brown stink bug; *Delia platura,* seedcorn maggot; *Mayetiola destructor,* Hessian fly; *Petrobia latens,* brown wheat mite; Oil Seed Rape: *Brevicoryne brassicae,* cabbage aphid; *Phyllotreta cruciferae,* Flea beetle; *Mamestra configurata,* Bertha armyworm; *Plutella xylostella,* Diamond-back moth; Delia ssp., Root maggots.

The method of the present invention comprises genetically transforming a plant to generate a hypersensitive-like response that is nonspecific for the invading pathogen. By "hypersensitive-like response" is intended a response whereby cells in immediate contact with the pathogen rapidly collapse and dry in a necrotic fleck, leading to a localized lesion mimicking that seen for the native plant-pathogen hypersensitive response. In accordance with the present invention, death of these cells, which is mediated by oxygen free radicals, results in limiting pathogen invasion to cells within the lesion area. By "nonspecific" is intended the hypersensitive-like response is triggered by any plant pathogen, as listed above, without the need for a gene-for-gene relationship between a resistance gene in the plant and a corresponding avirulence gene in the pathogen, as is required to illicit the native hypersensitive response.

As disclosed in the present invention, the method of generating a hypersensitive-like response to an invading pathogen comprises genetic manipulation of porphyrin levels within the cells that are in contact with the invading pathogen. In the native state, cell porphyrin levels are regulated in the C-5 porphyrin metabolic pathway. This pathway includes a series of enzymatic reactions that convert porphobilinogen, the immediate monopyrrole precursor to the porphyrins, to protoporphyrin IX, a cyclic tetrapyrrole precursor of heme-containing proteins. The pathway is important in both animals and plants for the eventual production of cytochromes, peroxidases, catalases, vitamin B12 and other corrins, and in the production of chlorophylls in plants. Important enzymes in this pathway include porphobilinogen deaminase (EC 4.3.1.8) and uroporphorinogen-III (co)synth(et)ase (EC 4.2.1.75), which enable condensation of 4 molecules of porphobilinogen to uroporphorinogen III; uroporphyrinogen decarboxylase (EC 4.1.1.37), which converts uroporphorinogen III to coproporphyrinogen III; coproporphyrinogen oxidase (EC 1.3.3.3), which converts coproporphyrinogen IE to protoporphyrinogen IX; and protoporphyrinogen oxidase (EC 1.3.3.4), which oxidizes protoporphyrinogen IX to protoporphyrin IX.

Mutations of human genes encoding enzymes in the porphyrin pathway result in a metabolic disorder that is generally called porphyria. This disorder is characterized by elevated levels of porphyrins in blood and urine. One consistent clinical manifestation of this disorder is skin sensitivity to light. In the case of porphyria cutanea tarda, intensely fluorescent, free uroporphyrin(ogen) HI is deposited under the surface of the skin. On exposure to light, easily photoexcitable uroporphyrin mi molecules readily react with oxygen to produce singlet oxygen and other reactive oxygen species that damage skin cells. This particular porphyria disorder is a result of mutations in the gene encoding uroporphyrinogen decarboxylase (urod gene). In humans, urod mutations inherit as mendelian dominants.

The urod gene and other genes involved in the porphyrin pathway have been highly conserved through evolution. Compositions of the present invention provide for the nucleotide sequence of a maize urod gene and a mutant phenotype, Les22, where one copy of the urod gene has become nonfunctional, causing phytoporphyria to develop. By "phytoporphyria" is intended a metabolic disorder in plants that is manifested by a lesion mimic phenotype that exhibits a dominant mode of inheritance similar to that found for mutations of the human urod gene that result in human uroporphyria. The maize urod nucleotide sequence, as well as nucleotide sequences for other urod genes and any other genes encoding enzymes of the C-5 porphyrin pathway, are useful in the method of the present invention.

In the method of the present invention, cell porphyrin levels are manipulated by stably transforming a plant with an antisense DNA nucleotide sequence for a targeted gene to inhibit expression of the targeted gene, where the targeted gene comprises the known DNA nucleotide sequence for one of the native genes encoding an enzyme of the C-5 porphyrin pathway. By "antisense DNA nucleotide sequence" is intended a sequence that is in inverse orientation to the 5' to 3' normal orientation of that nucleotide sequence. When delivered into a plant cell, the antisense DNA sequence prevents normal expression of the DNA nucleotide sequence for the native gene. The antisense nucleotide sequence encodes an RNA transcript that is complementary to and capable of hybridizing to the endogenous messenger RNA (MRNA) produced by transcription of the DNA nucleotide sequence for the native gene. Once bound to the endogenous MRNA, the antisense RNA product prevents production of the native enzyme involved in the porphyrin pathway. Depending upon the gene targeted for inhibition, specific porphyrin substrates can be targeted for accumulation.

These porphyrin substrates are photoexcitable, or photosensitive, and their accumulation in the presence of light brings about oxidative damage to cellular structural components. It is the accumulation of these substrates that will be manipulated in the present invention to bring about a hypersensitive-like response to pathogen invasion of a cell.

Use of antisense nucleotide sequences to inhibit or control gene expression is well known in the art. See particularly Inouye et al., U.S. Pat. Nos. 5,190,931 and 5,272,065; Albertsen et al., U.S. Pat. No. 5478369; Shewmaker et al., U.S. Pat. No. 5,453,566; Weintrab et al. (1985) *Trends Gen.* 1:22–25; and Bourque and Folk (1992) *Plant Mol. Biol.* 19:641–647. Antisense nucleotide sequences are particularly effective in manipulating metabolic pathways to alter the phenotype of an organism.

The antisense nucleotide sequence for any of the genes encoding the enzymes of the C-5 metabolic pathway that are involved in the production of protoporphyrin IX from delta-aminolevulinic acid may be used in the method of the present invention. Nucleotide sequences for a number of these genes are available in the art which include, but are not limited to, the sequenced genes encoding porphobilinogen deaminase (*Arabidopsis thaliana,* Accession No. X73535; *Euglena gracilus,* Accession No. X15743), uroporphyrinogen-III (co)synth(et)ase (yeast, Accession No. X04694), uroporphyrinogen decarboxylase (yeast, Accession No. X63721; barley, Accession No. X82832; tobacco, Accession No. X82833; maize, as disclosed in the present invention), coproporphyrinogen oxidase (soybean, Accession No. X71083; *Arabidopsis thaliana,* Accession No. T20727 for partial sequence), and protoporphyrinogen oxidase (yeast, Accession No. Z71381; barley, Accession No. Y13466; tobacco, Accession No. Y13465).

The invention encompasses isolated or substantially purified nucleic acid or protein compositions. More particularly, compositions of the present invention include isolated nucleic acid molecules comprising the nucleotide sequence for the naturally occurring maize urod gene (set forth in SEQ ID NO: 1), and fragments and variants thereof Compositions of the present invention also include the naturally occurring uroporphyrinogen decarboxylase (UROD) protein (whose sequence is set forth in SEQ ID NO: 2) encoded by this maize urod gene, as well as any substantially homologous and fimctionally equivalent variants thereof.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid molecule is free of sequences (preferably protein encoding sequences) that naturally flank the nucleic acid molecule (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid molecule is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably, culture medium represents less than about 30%, 20%, 10%, or 5% (by dry weight) of chemical precursors or non-protein-of-interest chemicals.

Fragments and variants of the native nucleotide and amino acid sequences are also encompassed by the present invention. By "fragment" is intended a portion of a nucleotide or amino acid sequence. Fragments of a nucleotide sequence may encode protein fragments that retain the biological activity of the native UROD protein, i.e., the sequence set forth in SEQ ID NO: 1, and hence confer UROD activity, which results in conversion of uroporphorinogen III to coproporphyrinogen III. Alternatively, fragments of a coding nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the entire nucleotide sequence encoding the UROD protein of the invention.

A fragment of a urod nucleotide sequence that encodes a biologically active portion of a UROD protein of the invention will encode at least 15, 25, 30, 40, 50, 75, 100, 150, 200, 250, 300, or 350 contiguous amino acids, or up to the total number of amino acids present in the full-length UROD protein of the invention (i.e., 394 amino acids; SEQ ID NO: 2). Fragments of a urod nucleotide sequence that are useflil as hybridization probes for PCR primers generally need not encode a biologically active portion of a UROD protein.

A biologically active portion of a UROD protein can be prepared by isolating a portion of the urod nucleotide sequence of the invention, expressing the encoded portion of the UROD protein (e.g., by recombinant expression in vitro), and assessing the activity of the encoded portion of the UROD protein. Nucleic acid molecules that are fragments of a urodnucleotide sequence comprise at least 15, 20, 50, 75, 100, 150, 200, 250, 300, 350, 400, 450, 500, 600, 700, 800,900, 1000, 1100, 1200, 1300, 1400, 1500, 1550, or 1600 nucleotides, or up to the number of nucleotides present in the full-length urod nucleotide sequence disclosed herein (i.e., 1604 nucleotides; SEQ ID NO: 1).

By "variants" is intended sequences having substantial similarity with a nucleotide sequence or protein disclosed herein. For nucleotide sequences, conservative variants include those sequences that, because of the degeneracy of the genetic code, encode the amino acid sequence of the UROD protein of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a UROD protein of the invention. Generally, nucleotide sequence variants of the invention will have at least 40%, 50%, 60%, 70%, generally, 80%, preferably 85%, 90% to 95%, even 98% or more sequence identity to the respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (2d ed., Cold Spring Harbor Laboratory Press, Plainview, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the UROD protein of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary MRNA structure. See EP Patent Application Publication No. 75,444.

Thus nucleotide sequences of the invention and the proteins encoded thereby include the naturally occurring forms as well as variants and fragments thereof. The variant nucleotide sequences and variant proteins will be substantially homologous to their naturally occurring sequence. A variant of a native nucleotide sequence or protein is "substantially homologous" to the native nucleotide sequence or protein when at least about 50%, 60%, to 70%, preferably at least about 80%, more preferably at least about 85%, 90%, and most preferably at least about 95%, to 98% of its nucleotide or amino acid sequence is identical to the native nucleotide or amino acid sequence. A variant protein will be functionally equivalent to the native protein. By "functionally equivalent" is intended that the sequence of the variant defines a chain that produces a protein having substantially the same biological effect as the native protein of interest. Thus, for purposes of the present invention, a functionally equivalent variant will confer UROD activity, which results in conversion of uroporphorinogen III to coproporphyrinogen III. Such functionally equivalent variants that comprise substantial sequence variations are also encompassed by the invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. Appl. Math.* 2:482; by the homology alignment algorithm of Needleman et al. (1970) *J. Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988)*Gene* 73:237–244 (1988); Higgins et al. (1989) *CABIOS* 5:151–153 ; Corpet et al. (1988) *Nuc. Acids Res.* 16:10881–90; Huang et al. (1992) *Computer Applications in the Biosciences* 8:155–65, and Person et al. (1994) *Methods of Mol. Biol.* 24:307–331; preferred computer alignment methods also include the BLASTP, BLASTN, and BLASTX algorithms (see Altschul et al. (1990) *J. Mol. Biol.* 215:403–410). Alignment is also often performed by inspection and manual alignment.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. to about 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 50, 55, or 60° C. However, nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleotide sequences encoding the enzymes of the porphyrin metabolic pathway can be the naturally occurring sequences or they may be synthetically derived sequences. Alternatively, the nucleotide sequence for the maize urod gene of the present invention, as well as previously published nucleotide sequences for other urod genes or other genes involved in the C-5 porphyrin metabolic pathway, can be utilized to isolate homologous genes from other plants, including Arabidopsis, sorghum, Brassica, wheat, tobacco, cotton, tomato, barley, sunflower, cucumber, alfalfa, soybeans, sorghum, etc.

Methods are readily available in the art for the hybridization of nucleic acid sequences. Coding sequences from other plants may be isolated according to well-known techniques based on their sequence homology to the maize urod coding sequence set forth herein or to other known coding sequences for other urod genes or for other genes in the porphyrin pathway. In these techniques, all or part of the known coding sequence is used as a probe that selectively hybridizes to other coding sequences for genes of the porphyrin pathway that are present in a population of cloned genomic DNA fragments or cDNA fragments (i.e., genomic or cDNA libraries) from a chosen plant.

For example, the entire maize urod gene sequence disclosed herein or portions thereof may be used as probes capable of specifically hybridizing to corresponding coding sequences and messenger RNAs. To achieve specific hybridization under a variety of conditions, such probes include sequences that are unique among urod coding sequences and are preferably at least about 10 nucleotides in length, and most preferably at least about 20 nucleotides in length. Such probes may be used to amplify urod coding sequences from a chosen plant by the well-known process of polymerase chain reaction (PCR).

Such techniques include hybridization screening of plated DNA libraries (either plaques or colonies; see, for example, Sambrook et al., eds. (1989) *Molecular Cloning: A Laboratory Manual* (2d ed., Cold Spring Harbor Laboratory Press, Plainview, N.Y.) and amplification by PCR using oligonucleotide primers corresponding to sequence domains conserved among the amino acid sequences (see, for example, Innis et al. (1990) *PCR Protocols, a Guide to Methods and Applications* (Academic Press, New York).

For example, hybridization of such sequences may be carried out under conditions of reduced stringency, medium stringency, or even stringent conditions (e.g., conditions represented by a wash stringency of 35–40% Formamide with 5×Denhardt's solution, 0.5% SDS, and 1×SSPE at 37EC; conditions represented by a wash stringency of 40–45% Formamide with 5×Denhardt's solution, 0.5% SDS, and 1×SSPE at 42EC; and conditions represented by a wash stringency of 50% Formamide with 5×Denhardt's solution, 0.5% SDS, and 1×SSPE at 42EC, respectively) to DNA encoding the wild-type maize urod gene disclosed herein in a standard hybridization assay. See Sambrook et al. (1989) *Molecular Cloning: A Laboratory Manual* (2d ed., Cold Spring Harbor Laboratory Press, Plainview, N.Y.). In general, sequences that code for a UROD protein and hybridize to the wild-type maize urod gene disclosed herein will be at least 40% to 50% homologous, about 60% to 70% homologous, and even 85%, 90%, 95% to 95% homologous or more with the maize sequence. That is, the sequence similarity of sequences may range, sharing at least about 40% to 50%, about 60% to 70%, and even at least about 80%, 85%, 90%, 95% to 98% sequence similarity. Generally, since leader peptides are not highly conserved between monocots and dicots, sequences can be utilized from the carboxyterminal end of the protein as probes for the isolation of corresponding sequences from any plant. Nucleotide probes can be constructed and utilized in hybridization experiments as discussed above. In this manner, even gene sequences that are divergent in the aminoterminal region can be identified and isolated for use in the methods of the invention.

Thus known nucleotide sequences or portions thereof for any urod gene, or any other gene encoding an enzyme in the C-5 porphyrin metabolic pathway, can be used as probes for identifying nucleotide sequences for similar genes in a chosen plant or organism. Once similar genes are identified, their respective antisense nucleotide sequences can be utilized in the present invention to inhibit or control expression of the genes encoding UROD or other enzymes of the C-5 porphyrin metabolic pathway. Although it is preferable to use the specific antisense nucleotide sequence corresponding to the nucleotide sequence for a targeted native urod gene, the antisense nucleotide sequence for the nucleotide sequence for any urod gene can be used in the invention to regulate the native urod gene. Likewise, the antisense nucleotide sequence for any alad gene can be used to regulate the targeted native alad gene of a plant; and so forth for all other genes associated with the pathway. In this manner, the degree of sequence homology between the gene serving as the template for the antisense nucleotide sequence and the targeted native gene will determine the degree of binding between the antisense nucleotide sequence and the nucleotide sequence for the targeted native gene. The greater the sequence homology, the greater the binding of the antisense sequence, and hence the greater the inhibition of expression of the targeted gene. In this manner, the degree of inhibition of specific enzyme activity, and hence accumulation of specific substrates to bring about the hypersensitive-like response to pathogen invasion, can be regulated.

Degree of suppression or inhibition of expression of the targeted gene may also be regulated by length of the antisense nucleotide sequence. Hence, the antisense nucleotide sequence can be designed to encode an RNA transcript that is complementary to and thus hybridizes to any portion of the endogenous mRNA produced by transcription of the DNA nucleotide sequence for the targeted native gene. That is, the hybridizing site may be proximal to the 5'-terminus or capping site, downstream from the capping site, between the capping site and the initiation codon, and may cover all or only a portion of the noncoding region, may bridge the noncoding and coding region, be complementary to all or part of the coding region, complementary to the 3'-terminus of the coding region, or complementary to the 3'-untranslated region of the mRNA. See particularly Shewmaker et al., U.S. Pat. No. 5453566; Inouye, U.S. Pat. No. 5,190,931; and Helene and Toulme, *Biochemica et Biophysica Acta* (1990):99–125. For the purposes of disease resistance, the antisense nucleotide sequence will encode an RNA product that hybridizes to about 50% of, preferably to about 75% of, more preferably to the entire endogenous mRNA, with the latter enabling maximum suppression of gene expression, and hence maximum hypersensitive-like response associated with accumulation of photoexcitable substrate.

The method of the present invention relies upon expression of the introduced antisense nucleotide sequence in response to pathogen invasion of a cell. Expression of the antisense sequence then effectively disrupts porphyrin metabolism such that photosensitive porphyrins accumulate. The presence of these porphyrins causes oxidative damage, leading to a hypersensitive-like response within the invaded cell and development of a localized lesion wherein the spread of the pathogen is contained.

Because expression of the introduced antisense DNA sequence in a plant cell causes cell death, an inducible promoter is used to drive expression of this sequence. The inducible promoter must be tightly regulated to prevent unnecessary cell death yet be expressed in the presence of a pathogen to prevent spread of the infection and disease symptoms. Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J Plant Pathol.* 89:245–254; Uknes et al. (1992) *Plant Cell* 4:645–656; and Van Loon (1985) *Plant Mol. Virol.* 4:111–116; and the copending applications both entitled "*Maize Inducible Promoters,*" U.S. Patent Application Serial No. 60/076,100, filed Feb. 26, 1998, and U.S. Patent Application Serial No. 60/079,648, filed Mar. 27, 1998; herein incorporated by reference.

Of particular interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Molecular and General Genetics* 2:93–98; and Yang (1996) *Proc. Natl. Acad. Sci. USA* 93:14972–14977. See also Chen et al. (1996) *Plant J.* 10:955–966; Zhang and Sing (1994) *Proc. Natl. Acad. Sci. USA* 91:2507–2511; Warner et al. (1993) *Plant J.* 3:191–201; Siebertz et al. (1989) *Plant Cell* 1:961–968; and the references cited therein. Of particular interest is the inducible promoter for the maize PRMS gene, whose expression is induced by the pathogen *Fusarium moniliforme* (see, for example, Cordero et al. (1992) *Physiological and Molecular Plant Pathology* 41:189–200).

The antisense nucleotide sequences for the native genes encoding enzymes involved in the C-5 porphyrin pathway are useful in the genetic manipulation of any plant when operably linked to an inducible promoter, more preferably a pathogen-inducible promoter. In this manner, the antisense sequences of the invention are provided in expression cassettes for expression in the plant of interest.

Such expression cassettes will comprise a transcriptional initiation region linked to the antisense nucleotide sequence for the native gene or genes targeted for inhibition. Such an expression cassette is provided with a plurality of restriction sites for insertion of the antisense sequence to be under the transcriptional regulation of the regulatory regions. The expression cassette may additionally contain selectable marker genes.

The transcriptional initiation region, the inducible promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to transcription initiation region that is heterologous to the coding sequence. The transcriptional cassette will include in the 5'-3' direction of transcription, a transcriptional and translational initiation region, an antisense DNA sequence for the targeted gene of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nuc. Acids Res.* 17:7891–7903; Joshi et al. (1987) *Nuc. Acid Res.* 15:9627–9639.

The antisense sequences of the invention are provided in expression cassettes for expression in the plant of interest. The cassette will include 5' and 3' regulatory sequences operably linked to the gene of interest. The cassette may additionally contain at least one additional gene to be cotransformed into the organism. Alternatively, the additional gene(s) can be provided on another expression cassette.

For example, flow of substrates into the porphyrin pathway is regulated by feedback inhibition of 5-aminolevulinic acid dehyratase (ALAD), which generates 2 molecules of porphobilinogen from 2 molecules of 5-aminolevulinic acid. For the antisense nucleotides of the present invention to be effective in generating a hypersensitive-like response, ALAD activity must be high enough to support accumulation of photoexcitable porphyrin substrates. This is achieved naturally in developing tissues, where the demand for protoporphyrin IX to support chlorophyll and heme synthesis is high. In developmentally mature tissues, demand for protoporphyrin IX is decreased, and ALAD activity is correspondingly decreased. To enable continued elevated activity, the expression cassette can also comprise a nucleotide sequence encoding the alad gene, which is also operably linked to the inducible promoter.

Where appropriate, the antisense sequence and additional gene(s) may be optimized for increased expression in the transformed plant. That is, these nucleotide sequences can be synthesized using plant-preferred codons for improved expression. Methods are available in the art for synthesizing plant-preferred genes. See, for example, U.S. Pat. Nos. 5,380,831, 5,436,391, and Murray et al. (1989) *Nuc. Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences, which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picomavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) *Molecular Biology of RNA,* pages 237–256); and maize chlorotic mottle virus leader (MCMV) (Lommel et al. (1991) Virology 81:382–385). See also Della-Cioppa et al. (1987) *Plant Physiology* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

The antisense nucleotide sequences of the present invention can be used to transform any plant. In this manner, genetically modified plants, plant cells, plant tissue, seed, and the like can be obtained. Transformation protocols may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055); direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact *Plant Cells* via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou et al. (1995) *Annals of Botany* 75:407–413 (rice); Osjoda et al. (1996) *Nature Biotech.* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The methods of the invention can be used with other methods available in the art for enhancing disease resistance in plants.

The antisense nucleotide sequences of the present invention also find use in targeting specific tissues for cell death. In this manner, a plant of choice can be stably transformed with an expression cassette comprising a chimeric gene that comprises an antisense nucleotide sequence for a gene encoding an enzyme in the C-5 porphyrin metabolic pathway, wherein the antisense sequence is operably linked to a stamen promoter to achieve male sterility. In this manner, a promoter that normally enables stamen development now drives expression of the antisense sequence, whose expression ultimately leads to cell death in tissues that normally would have become fertile stamens. Such promoters are available in the art (see, for example, EPA0344029 and U.S. Pat. No. 5,470,359, herein incorporated by reference).

In another embodiment of the present invention, a method for overcoming herbicide resistance during crop rotation is provided. Following harvest of a first crop of the season, herbicide treatment may routinely be used to eliminate unwanted weeds during preparation of the field site for a subsequent crop of the season. However, this herbicide application is ineffective at removing volunteer plants of the first crop, which may be overlooked during field preparation or which may germinate from previously buried or dispersed seed. An abundance of these volunteer plants effectively poses competition for environmental resources similar to that seen with weeds, and hence has the potential to decrease yield of the subsequent crop.

The antisense nucleotide sequences of the present invention are useful in overcoming this problem. Herbicide resistant crop plants can be stably transformed with an expression cassette comprising a chimeric gene that comprises an antisense nucleotide sequence for a gene encoding an enzyme in the C-5 porphyrin metabolic pathway. For the purpose of overcoming herbicide resistance, the antisense nucleotide sequence is operably linked to a chemical-inducible promoter, such that contact of the plant with a known chemical substance induces expression of the antisense nucleotide sequence. As before, expression of this sequence results in accumulation of photosensitive porphyrins, ultimately leading to photooxidative damage to cell membranes and death of the plant tissues.

Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid.

In this manner, seed of the transformed crop plants, and transformed seedlings germinating therefrom, would effectively die following application of the chemical substance whose inducible promoter is part of the stably incorporated chimeric gene. Following harvest of the desired crop product, the remaining plant parts can be treated with an application of the chemical substance. Furthermore, any volunteer seedlings germinating from seed can be similarly treated to eliminate the undesired crop from the field.

The invention further finds use in therapies for mammals, particularly humans, for preventing growth of malignant cells. In this embodiment of the present invention, a method for killing, and thereby preventing the proliferation of, malignant or nonmalignant abnormal cells in an affected tissue is provided. The antioxidant defense capabilities of these abnormal cells, particularly malignant cancer cells, are compromised relative to normal cells. By "antioxidant" is intended the ability to keep photosensitive compounds, such as tetrapyrrole-containing porphyrins, and other reactive oxygen species, including hydrogen peroxide, at relatively low cellular concentrations to prevent oxidative damage to cell membranes. These normal defense capabilities include tight regulation of the C-5 porphyrin pathway and the presence of catalases and peroxidases, which are heme-containing enzymes. Thus, manipulation of the C-5 porphyrin pathway to disrupt an already compromised defense capability would be an effective means of preventing further proliferation of these abnormal cells.

In accordance with this method, a pharmaceutical composition comprising an antisense nucleotide sequence complementary to the mRNA for any one of the human genes encoding the key enzymes outlined in the C-5 porphyrin pathway can be administered to the affected tissue in such a manner as to target the proliferating abnormal cells. Human genes encoding these enzymes have been identified and sequenced and are well known in the art. Once at the targeted site, the antisense nucleotide sequence will hybridize to mRNA of the targeted gene of the C-5 pathway, effectively blocking transcription, leading to accumulation of photosensitive porphyrin substrate. Subsequent exposure of the treated tissue to light of photoactivating wavelengths in the visible region for an experimentally determined length of time would lead to photooxidative damage and death of the treated cells.

Antisense nucleotide sequences that are directly complementary to the targeted mRNA transcripts include not only the native polymers of the biologically active nucleotides, but also sequences that are modified to improve stability and/or lipid solubility. Modifications, such as substitution of methyl or sulfur groups in the internucleotide phosphodiester linkage, can be used to improve lipid solubility and prevent nuclease cleavage of the antisense sequence, thereby effectively increasing availability of the sequence for hybridization to mRNA.

Such antisense oligonucleotides may be oligonucleotides wherein at least one, or all, of the internucleotide bridging phosphate residues are modified phosphates, such as methyl phosphonates, methyl phosphonothioates, phosphoromorpholidates, phosphoropiperazidates and phosphoramidates. For example, some, for example, every other one, of the internucleotide bridging phosphate residues may be modified as described. In another example, such antisense oligonucleotides are oligonucleotides wherein at least one, or all, of the nucleotides contain a 2 loweralkyl moiety (e.g., C1–C4, linear or branched, saturated or unsaturated alkyl, such as methyl, ethyl, ethenyl, propyl, 1-propenyl, 2-propenyl, and isopropyl). See also Furdon et al. (1989) *Nucleic Acids Res.* 17:9193–9204; Agrawal et al. (1990) *Proc. Natl. Acad. Sci. USA* 87:1401–1405; Baker et al. (1990) *Nucl. Acids Res.* 18:3537–3543; Sproat et al. (1989) *Nuc. Acids Res.* 17:3373–3389; Walder et al. (1988) *Proc. Natl. Acad. Sci. USA* 85:5011–5015.

Modification of the phosphodiester backbone has been shown to impart stability and may allow for enhanced affinity and increased cellular penetration of ODNs. Additionally, chemical strategies may be employed to replace the entire phosphodiester backbone with novel linkages. Phosphorothioate and methylphosphonate modified ODNs may be made through automated ODN synthesis. A phosphorodithioate version of the phosphorothioate can be synthesized. In the dithioate linkage, the nonbridging oxygens can be substituted with sulfur. This linkage is highly nuclease resistant.

Sugar modifications may also be used to enhance stability and affinity of the molecules. The alpha-anomer of a 2'-deoxyribose sugar has the base inverted with respect to the natural beta-anomer. ODNs containing alpha-anomer sugars are resistant to nuclease degradation.

This method of treatment depends upon successful delivery of the pharmaceutical composition comprising the antisense nucleotide sequence to the targeted cells, with limited accumulation in cells of normal tissue. In the event that normal cells accumulate the pharmaceutical composition, exposure to light following treatment should be minimized. However, unlike other cancer treatment methods that rely upon systemic doses of exogenous porphyrins, such as hemotoporphyrin IX or hematoporphyrin derivatives, this method relies on accumulation of naturally occurring porphyrins in the targeted abnormal cells. The residence time of naturally occurring porphyrins is greatly reduced (on the order of days) when compared to residence time of exogenous porphyrins (on the order of weeks ), so that photosensitive levels do not persist for long periods following treatment. This greatly reduces the risk of photosensitivity of treated tissues.

Additionally, this method relies upon the presence of 5-aminolevulinic acid (ALA) as a precursor for porphyrin production. This substrate is regulated by tight feedback inhibition of the C-5 porphyrin metabolic pathway. As an alternative, additional amounts of ALA can be administered separately or with the pharmaceutical composition comprising the antisense nucleotide sequence.

The present invention also provides a maize lesion mimic phenotype, designated Les22, that represents a dominant mutant situation whose molecular basis resides in the disruption of the maize urod gene disclosed herein. In Les22 individuals, one copy of the urod gene comprises at least one Mutator (Mu) transposable element inserted within its nucleotide sequence. This insertion results in a null mutation within this copy of the gene. By "null mutation" is intended a mutation that results in loss-of-function of the gene. Thus Les22 individuals have one copy of the urod gene that is nonfunctional. For example, in the maize lesion mimic mutant designated Les22-7, the nonfunctional copy of the urod gene has aMu transposable element inserted between bp 102 and bp 103 of the nucleotide sequence set forth in SEQ ID NO: 1, and in the maize lesion mimic mutant designated Les22-3, the nonfunctional copy of the urod gene has a Mu transposable element inserted between bp 196 and bp 197 of SEQ ID NO: 1. In Les22 lesion mimics, the single functional copy of urod produces an insufficient amount of UROD protein, leading to a partial block in the porphoryin metabolic pathway that results in accumulation of this enzyme's substrate, uroporphoryin III. Accumulation of this highly photoreactive substrate leads to development of phytophoria in the presence of photoactivating wavelengths in the visible region.

The maize lesion mimic mutant phenotype Les22 and its molecular basis as disclosed in this invention are novel in the plant kingdom. The implications of this novelty are significant for purposes beyond the methods of the present invention. First, being the first identified mutation of the porphyrin pathway in plants, Les22 provides an excellent tool to understand how the production of chlorophyll and heme is regulated.

Second, this apparently represents the first case of a mutation of a conserved gene that has parallel phenotypic manifestations in both humans and plants. The dominant nature of this defect suggests that the porphyrin pathway, which although is expected to operate in different subcellular locations in plant and human cells, is regulated very similarly in both organisms. Since mutations of most genes of the porphyrin pathway in humans result in porphyria, one consistent clinical manifestation of which is heightened skin sensitivity to light, mutations with a phenotype like that of Les22 may also result from defects in other genes of the porphyrin pathway in plants. In fact, genetic allelism tests between various Les22-mutants support this hypothesis.

Third, the dominant nature of Les22 is caused not by a gain of a new function, but rather is the result of a null, loss-of-function mutation in one copy of the urod gene. This represents a rare, if not the only, case of haplo-insufficiency (gene dosage dependence) in plants. Haplo-insufficiency, which has been well established in the case of human uroporphyria, is thought not to exist in plants (Birchler (1993) *Annu. Rev. Genet.* 27:181).

Fourth, Les22, being cell autonomous, visually discernible, and nonlethal, provides an elegant molecular tool to probe into the phenomenon of Mu suppression in maize. This enigmatic phenomenon seems to epitomize the mechanism(s) by which plants keep the activity of transposons in check. The phenotypic effects of certain mutations caused by Mutator (Mu) insertions sometimes become dependent on the activity of the Mu system. For example, the mutant phenotype of a mutation will express if the plant has Mu activity. However, when Mu turns off, the mutant phenotype reverts back to the normal wild-type phenotype, and this happens without the loss of the Mu insertion. Such mutations, and the phenomenon they exhibit, are called Mu suppressible. What causes a plant to lose Mu activity remains enigmatic, but it often happens during vegetative development of the plant as well as following inbreeding, even though intact Mu elements remain in the plant. At the DNA level, Mu elements of plants with the suppressed mutant phenotype show hypermethylation.

This phenomenon of dominant negative regulation was first uncovered with hcf-106 (Martienssen et al. (1990) *Genes Dev.* 4:331–343) and later shown to suppress coordinately the phenotypes of both hcf-106 and Les28 (a lesion mimic mutant phenotypically identical to Les22) (Martienssen and Baron (1994) *Genetics* 136:1157–1170). A few alleles of Les22, including Les22-7, are also Mu-suppressible.

Finally, from a practical viewpoint, Les22 may provide a simplified system for the development of effective sunscreens needed to protect human skin from high-intensity light and UV damage. Cell lines, or plants, that have been transformed with expression cassettes comprising an antisense nucleotide sequence for a urod gene or other gene encoding an enzyme of the C-5 pathway can be used to test for effectiveness of sunscreens. In this case, antisense sequences may be operably linked to an inducible promoter, such as a chemical inducible promoter, as previously described. These cell lines, or plants, can be administered the chemical inducer in the presence of putative sunscreen substances, and treated cell lines or plants can subsequently be exposed to light of photoactivating wavelengths. Effectiveness of a putative sunscreen can be measured in terms of its ability to prevent photooxidative damage to the cells. By "photooxidative damage" is intended loss of cellular functions, such as loss of membrane integrity and normal function of organelles, including cell death. This damage results from the interaction of intercellular components with reactive oxygen species, which are the reaction products of photoreactive substrates, such as the photosensitive porphyrins, and oxygen in the presence of photoactivating wavelengths. Thus, in the case of a test plant, an effective putative sunscreen composition would, for example, prevent development of necrotic spots and lesions on the treated leaf tissue. Alternatively, a plant assay system with a Les22 phenotype (e.g., maize Les22 seedlings) may be used to rapidly screen a large number of potential sunscreen creams or compositions. Since the Les22 phenotype is completely dependent on irradiation, the effectiveness of various creams can be rapidly determined, where application of an effective sunscreen composition to a leaf would prevent the Les22 phenotype, i.e., lesions, from developing during exposure to light of photoactivating wavelengths, such as wavelengths of normal sunlight.

The following examples are offered by way of illustration and not by way of limitation.

EXPERIMENTAL

To elucidate the molecular basis of a dominant lesion mimic mutation of maize, Les22 (previously designated Les*-2552; see Johal (1994) *Maydica* 89:69), which is characterized by the formation of discrete, tiny whitish-gray bleached or necrotic spots on leaf blades that partly resemble hypersensitive response lesions in appearance, was selected. Like most lesion mimics of maize, the expression of Les22 lesions is cell autonomous, developmentally dictated, and light-dependent (Johal (1994) *Maydica* 39:69). Lesions do not initiate on leaf regions that are protected from the light. However, lesions form in the albino sectors of double mutants of Les22 with ijl , a recessive mutation characterized by alternate green and albino leaf stripes (Han et al. (1992) *EMBO J.* 11:4037), suggesting that the expression of Les22 lesions is mediated primarily by incident light. Two other mutations that exhibit a phenotype identical to Les22 are Les2 (Neuffer et al. (1975) *J. Hered.* 66:265) and Les28 (Martienssen et al. (1994) *Genetics* 136:1157). Interestingly, Les22, like Les2, maps to the short arm of chromosome 1. The map location of Les28 has not been reported yet, although some mutant alleles of Les22, including Les22-7 (see below), exhibit a Mu-suppressible phenomenon previously described for Les28.

EXAMPLE 1

Plant Material

The first Les22 mutant that allowed us to define the Les22 locus was a gift from Dr. Don Robertson of Iowa State University. It had appeared spontaneously in one of his Mutator nurseries. This mutant has been designated as Les22-17.

All other Les22 mutants, Les22-1 through Les22-16, with the exception of Les22-7, were recovered from various Mutator populations at the Pioneer nurseries. These Mutator populations were generated in the laboratory either to tag various genes, including Hm1, Br2, Lls1, and Bk2, by directed mutagenesis or to identify new mutant phenotypes of interest by developing random F2 populations.

The Les22-7 mutant, which allowed Les22 to be cloned, was isolated at the University of Missouri in 1993. The progeny from which it was isolated as a single event was developed at the Pioneer Winter Nursery in Hawaii in 1989 as follows. A plant from the row HW89-37-326#3, with the genotype Pr1×CSH89-9-8-1, was pollinated with pollen from the inbred Pr1.

The source of all Mutator stocks that happened to generate Les22 was a laboratory at Pioneer Hi-Bred. Original Mutator material was received from Dr. Don Robertson, Iowa State University.

EXAMPLE 2

Determination of Les22 Homozygous Phenotype

An outcross progeny of Les22-9 with A632 was used to map a number of RFLP markers from the short arm of chromosome 1 to determine what would be the phenotype of a plant homozygous for Les22. Two RFLP markers, UMC194 and UMC76, were identified that mapped 2.6 cM distal and 9.8 cM proximal to Les22, respectively. These markers were used to genotype an F2 population derived from a Les22 mutant. Contrary to what was thought previously (Johal (1994) Maydica 39:69), densely lesioned F2 plants were not homozygous for Les22. Instead, a yellow seedling lethal (ysl) plant that scalded easily in sunlight was found to segregate completely with both the flanking RFLP markers, raising the possibility that this ysl may very well be the phenotype of a Les22 homozygote.

EXAMPLE 3

Cloning of the Mutant Les22 Gene

To clone Les22, a Mutator (Mu) transposon-based gene tagging approach was used that relied on the random appearance of this mutant phenotype in various Mu populations (Johal (1994) Maydica 39:69–76). Being a dominant mutation, Les22 was easy to spot even in populations other than F2s, and as a result, 16 cases of independent origin, designated Les22-1 through Les22-16, were collected. To identify Mu elements that may have caused these mutations, each mutant was backcrossed three times with either B73 or A632 (Johal (1994) Maydica 39:69–76), and the progeny from the last cross was subjected to a gel-blot-based analysis that examined the linkage of each of the nine Mu elements with each mutant allele (Walbot (1992) Annu. Rev. Plant Physiol. Plant Mol. Biol. 43:49–82; Bennetzen et al. (1993) Crit. Rev. Plant Sci. 12:57–95).

Genomic DNA from maize seedlings was extracted by the CTAB-based method as previously described (Hulbert et al. (1991) Mol. Gen. Genet. 226:377–382). Southern blot analysis to identify RFLP markers and to perform cosegregation analysis was done as previously described (Gardiner et al. (1993) Genetics 134:917–930). Cosegregation analysis, to look for Mu elements linked to various Les22 mutant alleles, was first performed with pooled (involving at least 15 plants) DNAs from either the mutant or wild-type siblings of each mutant. DNA samples were digested with seven restriction enzymes, and the blots were hybridized with each of the nine Mu elements as described earlier (Gray et al. (1997) Cell 89:25–31).

From the Les22-7 family, a Mu1-hybridizing 6.5 kb Xho I restriction fragment was identified that was present in the DNA of all 39 mutants and absent in the DNA of all 27 wild-type sibs (data not shown), suggesting that this restriction fragment either carries at least a part of the Les22 gene or contains a Mu1 element that is closely linked to it. This restriction fragment was cloned in λ Zapil vector (Stratagene), followed by rescuing of this fragment as a phagemid using in vivo excision.

EXAMPLE 4

PCR Verification of Cloned Les22 Gene

To verify the cloning of Les22, a PCR approach was used (Gray et al. (1997) Cell 89:25). A 500 bp fragment flanking on the left side of Mu1 insertion in this clone, designated LF7, was amplified using a Mu-TIR primer (SEQ ID NO: 3) (Gray et al. (1997) Cell 89:25) and the reverse primer from the 6.5 kb Xho I clone. LF7 was then subcloned in the TA cloning vector (Invitrogen) and then sequenced. Two oppositely orienting PCR primers were designed from the sequence of LF7 and each was used in combination with the Mu-TIR primer in a PCR reaction in which the template DNA was derived from each of the 16 Les22 mutants. The primer sequences were LF7-A (see SEQ ID NO: 4) and LF7-B (see SEQ ID NO: 5). Conditions for the PCR were as previously described (Gray et al. (1997) Cell 89:25).

A 300 base-pair amplification product, which hybridized with LF7, was obtained from the DNA of the Les22-3 mutant, demonstrating that a Mu element was present in the vicinity of the LF7 region in this mutant allele. Subsequent sequence analysis of this PCR product revealed that a Mu element had inserted in the Les22-3 mutant allele 95 nucleotides away from the Mu1 insertion in Les22-7. Multiple insertions of this sort in independent mutants are considered a proof for the correct cloning of a gene (Gray et al. (1997) Cell 89:25).

EXAMPLE 5

DNA Polymorphism and Northern Analysis

Unequivocal evidence that Les22 had been cloned came from two additional experiments. First, to detect polymorphism between the Les22-7 mutant allele (which was found from a single plant in the progeny of a cross between Pr1(an inbred) and a Mu active line) and its wild-type progenitor, DNA from 50 wild-type siblings of the original Les22-7 mutant was compared with the DNA of the Les22-7 mutant allele from one of the advanced generations of Les22-7 with A632 mentioned in the text. Respective DNAs were digested with Xba I, which does not cut within Mu1, and the blot was hybridized with LF7. Examination of the DNA blot revealed a restriction fragment length polymorphism, with the size difference between the band for the wild-type progenitor allele and the upper band for the mutant allele of Les22-7 being 1.4 kb (data not shown). This DNA polymorphism is of the size expected from a Mu1 insertion (Bennetzen et al. (1993) Crit. Rev. Plant Sci. 12:57).

Second, RNA extraction and subsequent Northern analysis was performed as described previously (Johal and Briggs (1992) Science 258:985), except that total RNA (30 µg per lane) was used in this study. The entire cDNA was used as a probe. Northern analysis showed that the steady-state level of a 1.5 kb transcript, which was found fairly abundantly in wild-type plants, was reduced to about 50% of the wild-type level in the Les22 alleles of not only Les22-3 and Les22-7 (both of which are caused by Mu insertions), but also of Les22-15 (data not shown). Furthermore, this transcript was completely missing in the ysl mutants that segregated recessively in the self-pollinated populations of each of Les22-3, Les22-7, and Les22-15, confirming that the ysl phenotype constitutes the homozygous form of Les22. Additionally, these results indicate that all three of the mutant alleles characterized here by Northern analysis are the result of null mutations of Les22.

EXAMPLE 6

Determination of the Molecular Nature of Les22

To ascertain the molecular nature of Les22, a 1.5 kb cDNA clone corresponding to the sequence of LF7 was recovered from the maize EST collection at Pioneer Hi-Bred International, Inc., and sequenced. DNA sequences were determined by automated sequencing on an ABI377 sequencer (Perkin Elmer) situated at the DNA Core Facility of the University of Missouri. DNA sequence analysis was performed using ALIGN and MEGALIGN programs of the DNASTAR software package (DNASTAR Inc., Madison, Wis.). Searches of the GenBank database were performed using the National Center for Biotechnology Information's BLAST WWW Server.

Blast analysis indicated that Les22 encodes uroporphyrinogen decarboxylase (UROD), the fifth enzyme of the porphyrin pathway that is required in plants to produce the tetrapyrrole rings of both chlorophyll and heme. The cDNA sequence for the maize urod gene is set forth in SEQ ID NO: 1. Consistent with this revelation is the observation that plants homozygous recessive for Les22 exhibit a chlorophyll-less ysl phenotype. Les22 mutants also appear to be deficient in heme. Protein extraction and catalase activity assays were carried out as previously described (Anderson et al. (1995) *Plant Physiol.* 109:1247) for wild-type (Wt), Les22 mutant (M), and ysl (Y) plants. Protein concentration was quantified using a protein assay kit (Bio-Rad) and 30 μg total protein was loaded per lane. Four units of catalase (Sigma) were loaded in the control lane. Catalase activity, which depends on a heme prosthetic group, is significantly reduced and eliminated in Les22 mutants and homozygotes, respectively, as compared to the level detected in wild-type siblings (data not shown).

The urod gene and the porphyrin pathway, in which UROD catalyzes the sequential decarboxylation of uroporphyrinogen III to coproporphyrinogen imi (Elder and Roberts (1995) *J. Bioener. Biomem.* 27:207–214; von Wettstein et al. (1995) *Plant Cell* 7:1039–1057), have been highly conserved through evolution (see, for example, Jordan, ed. (1991) in *Biosynthesis of Tetrapyrroles* (Elsevier Science Publishers), pages 1–66; Labbe-Bois et al. (1977) *Mol. Gen. Genet.* 156:177; Chamnongpol et al. (1996) *Plant J.* 10:491; Zoladek et al. (1996) *Photochem. Photobiol.* 64:957). Not unexpectedly therefore, the predicted protein of the maize urod gene (set forth in SEQ ID NO: 2) exhibits a 97%, 93% and 54% amino acid similarity to the corresponding proteins from barley, tobacco, and humans, respectively (Romeo et al. (1986) *J. Biol. Chem.* 261:9825; Mock et al. (1995) *Plant Mol. Biol.* 28:245). Compared to the 391 amino acid protein of tobacco, the maize urod gene translates into a protein of 393 amino acids, the first 62 amino acids of which, like the 60 amino acids of the tobacco UROD but from which it has diverged significantly, may constitute the transit peptide that is expected to localize the enzyme in the chloroplast (Mock et al. (1995) *Plant Mol. Biol.* 28:245). In the mutant alleles of Les22-7 and Les22-3, Mu elements had inserted between bp 102 and bp 103 and between bp 196 and bp 197, respectively, of the nucleotide sequence for the maize urod gene set forth in SEQ ID NO: 1. Thus insertion of the Mu elements was 34 nucleotides upstream and 59 nucleotides downstream, respectively, from the first nucleotide (bp 137 of SEQ ID NO: 1) of the ATG start codon. The locations of both of these Mu insertions are critical and are expected to cause null mutations in the Les22 gene, as has been demonstrated by the transcript analysis. In addition, the location of the Mu1 element in Les22-7, which appears to be between the transcription and translation start sites of urod, is consistent with what has been found previously with Mu-suppressible mutants whose phenotypic manifestations are dependent on Mu activity (Barkan et al. (1991) *Proc. Natl. Acad. Sci. USA* 88:3502–3506).

Accepting that Les22 results from a disruption of urod, how does this deficiency lead to a lesion mimic phenotype that exhibits a dominant mode of inheritance? A compelling explanation emerges from the examination of urod mutations in humans which, like Les22, inherit as mendelian dominants, are dependent on light for phenotypic manifestations, and result from a loss-of-function of the urod gene (Romeo (1977) *Hum. Genet.* 39:261–276; De Vemeuil et al. (1986) *Science* 234:732–734; Moore et al. (1987) *Disorders of Porphyrin Metabolism* (Plenum Publishing Corp., New York). These urod defects are responsible for a metabolic disorder called porphyria cutanea tarda. As previously mentioned, the major clinical manifestation of this defect is hypersensitivity of skin to the damaging effects of sunlight, apparently caused by the excessive accumulation of easily photoexcitable uroporphyrin III (Moore et al. (1987) *Disorders of Porphyrin Metabolism* (Plenum Publishing Corp., New York); Straka et al. (1990) *Annu. Rev. Med.* 41:457–469; Moore (1993) *Int. J. Biochem.* 25:1353–1368; McCarrol (1995) *Analytical Chem.* 67:425R-428R). The reason for this manifestation is that when an allele of the urod gene becomes inactive as a result of a null mutation, the activity of UROD is reduced to one half of its normal level, leading to a partial block in the porphyrin metabolic pathway and resulting in uroporphyrin accumulation. On exposure to light, excited uroporphyrin, like all other porphyrin intermediates, readily reacts with oxygen to produce singlet oxygen and other reactive oxygen species that damage skin cells (Moore et al. (1987) *Disorders of Porphyrin Metabolism* (Plenum Publishing Corp., New York); Straka et al. (1990) *Annu. Rev. Med.* 41:457–469; Zoladek et al. (1996) *Photochem. Photobiol.* 64:957–962).

Several features of Les22 suggests that it has much in common with human porphyria cutanea tarda and may therefore be caused by the same mechanism. For instance, the phenotypic manifestation of both Les22 and porphyria is conditioned by sunlight. They both inherit as dominant mutations, and this dominance is not the result of a gain of a new function, as is usually the case with most dominant mutations (Hodkin (1993) *Trends Genet.* 9:1–2), but is the consequence of a loss of function of one copy of the urod gene.

To evaluate whether the pathologic basis of Les22 also has its roots in porphyria, uroporphyrin(ogen) and its natural product, coproporphyrin(ogen), were extracted from both Les22 heterozygotes (with the lesion mimic phenotype) and homozygotes(ysl mutants) and compared with those of their Wt siblings. Extractions were obtained from 10 day-old maize seedlings of an F2 population of Les22-15. The methods used to extract and HPLC analyze these porphyrin intermediates were as previously described (Mock and Grimm (1997) *Plant Mol. Biol.* 28:245–256; and Kruse et al. (1995) *EMBO J.* 14:3712–3720). The entire foliar tissue (pooled) was used forysl mutants. For Les22 mutants (heterozygotes), only the second leaf (from the bottom), partitioned into lesion-containing (apical) and lesion-lacking (bottom) parts and pooled from a number of plants, as used. Pooled tissues from Wt siblings were equivalent to the corresponding tissue from Les22 mutants. Compared to Wt controls, uroporphyrin levels were found to be elevated in Les22 plants. While Les22 mutants exhibited a 2- to 3-fold increase in uroporphyrin levels (Table 1), as would be expected from their heterozygous genotype with only one functional copy of the urod gene, Les22 homozygotes had as much as 60 times the amount of uroporphyrin as compared to Wt siblings (Table 1). In contrast, no such increases in coproporphyrin were detected in either of the Les22 genotypes (data not shown). These results are consistent with the interpretation that the porphyrin pathway is partly blocked at the step catalyzed by UROD in the Les22 lesion mimic mutants, and that this disorder is responsible for the etiology of Les22. Supporting this conclusion is the finding that tobacco transgenics over-expressing antisense urod, besides showing stunted growth, exhibited light-dependent induction of necrotic leaf lesions, the intensity of which correlated with the reduction of UROD activity (Mock and Grimm (1997) *Plant Physiol.* 113:1101). Table 1. Uroporphyrin III levels in the leaf tissues (apical, basal, or whole) of a Les22 mutant, its homozygote (ysl), and a WT (wild-type) sibling. The data presented represent the mean of four replications.

| Tissue | Uroporphyrin III (nmol/g fresh wt) |
|---|---|
| WT apical | 0.259 ± 0.008 |
| WT basal | 0.216 ± 0.005 |
| Les22 apical | 0.608 ± 0.018 |
| Les22 basal | 0.476 ± 0.014 |
| ysl total leaf | 14.042 ± 0.421 |

EXAMPLE 7

Characterization of Disease Resistance

Seeds of Les22-7 were segregating for Les22 and wild-type phenotype. They were planted in 8.89-cm pots in Strong-Lite Universal Mix potting soil (Universal Mix, Pine Buff, Ariz.) and grown in a greenhouse (16-h day, 20 to 35° C., 50% relative humidity, 0.56 to 0.62 mE s$^{-1}$ m$^{-2}$ of light from both the sun and halogen lamps). Plants were grown to the V-9 stage (see Simmons et al. (1998) *Mol. Plant-Microbe Interact.* 11:1110–1118). At this stage, plants expressing the Les22 phenotype had leaf 10 and older leaves completely covered with lesions. Leaf 11 of these plants had a basal portion that was lesion free; the middle of leaf 11 represented a zone where lesions were initiating; and the tip of leaf 11 had fully formed lesions. The upper leaf 13 was completely free of lesions.

A Texas isolate of *C. heterostrophus* (Drechs.) from a flngal culture collection was used to assay for corn leaf blight. Ten microliters of spore suspension (2×10$^4$ conidia/ mL) in 0.02% Tween 20 were placed on sterile, 6 mm-diameter filter paper disks (Whatman #1). Using transparent, polyethylene adhesive tape (3M), the disks were attached to the abaxial surface of the basal, middle, or tip of the blade on both sides of the mid-vein of leaf 11 and the middle of leaf 13. Plants were covered with plastic bags for the first 18 hours after inoculation, after which, both bags and tape squares were removed. Control plants received the same treatment but without spores. Plants received standard greenhouse care and were evaluated for development of symptoms 10 days after inoculation. Lesions were traced onto clear plastic film, digitized, and total lesion area/ inoculation site determined.

Conjugates of salicylic acid (SA) were extracted and quantified after chemical (base followed by acid) hydrolysis (Enyedi et al. (1992) *Proc. Natl. Acad. Sci. USA* 89:2480–2482). Samples were analyzed with a liquid chromatography system (Waters Corp., Milford, Mass.). Ten microliters of each extract were injected at a flow rate of 1.5 mL/min into a Luna 3 μm C-18 column (4.6 cm×100 mm; Phenomenex, Torrance, Calif.). The column was maintained at 40° C. and equilibrated in 22% acetonitrile against 78% of 0.1% citrate buffer, pH 3.3. Salicylic acid was eluted isocratically under these conditions (Rt,3.1 min) and quantified using a scanning fluorescence detector (Model 474, Waters Corp.) using excitation and emission wavelengths of 300 and 405 nm, respectively. The identity of SA in maize extracts was confirmed by its co-elution with authentic standard and by analysis of its UV light absorption spectrum, as measured with a photodiode array detector (Model 996, Waters Corp.).

When compared to wild-type siblings, plants expressing Les22 show enhanced resistance against infection by *C. heterostrophus* (FIG. 1). Resistance is not only manifested in leaf tissue that at the time of inoculation expresses a Les22 phenotype but also in younger tissue that has not formed any lesions.

Figure 2:
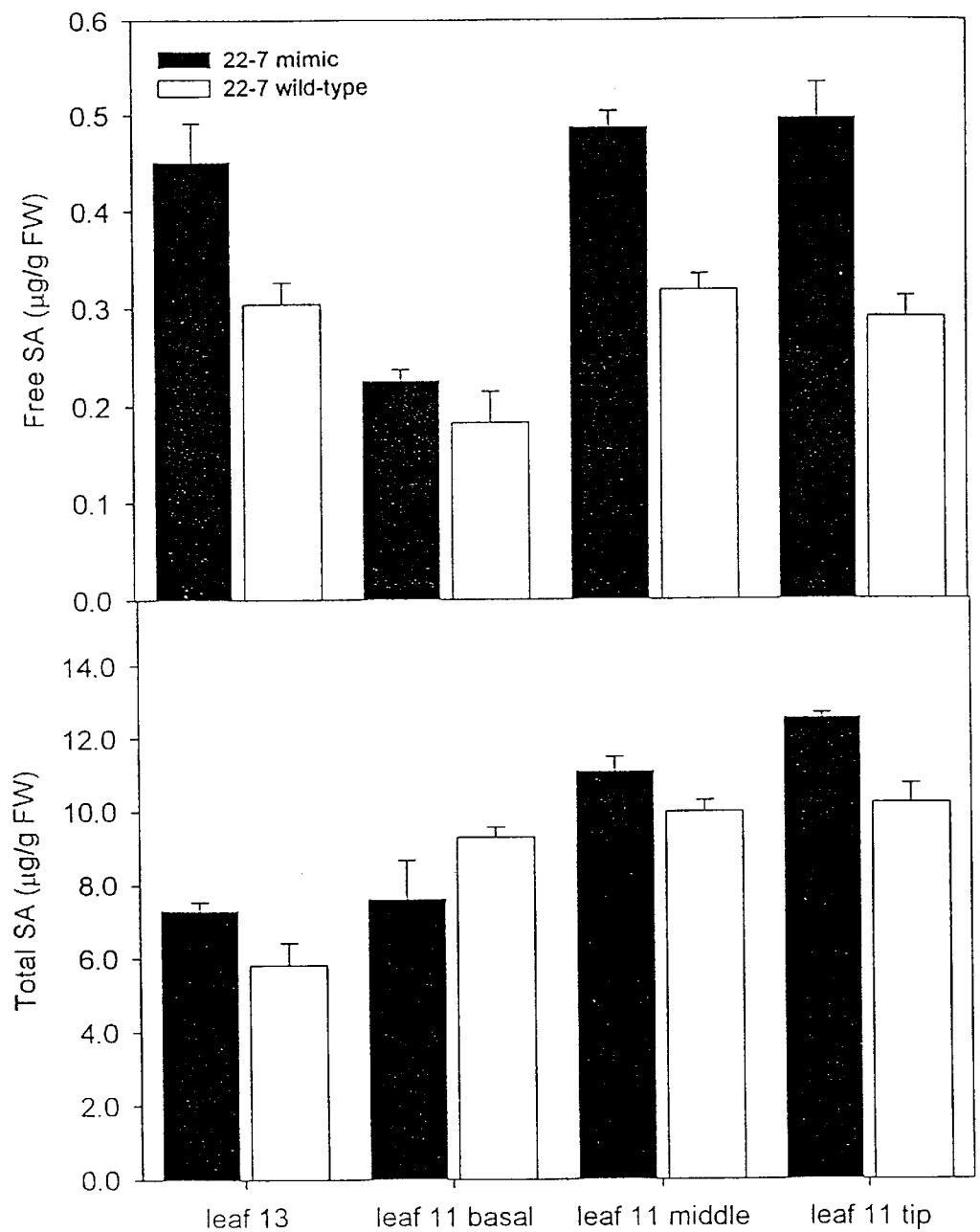
FIG. 2 shows the effect of Les22 and position of leaf tissue on levels of free and total salicylic acid in uninoculated plants. Leaves of Les22 are compared to wild-type leaves. Results shown represent the mean ±SEM for four determinations per tissue type pooled from three plants.

Levels of free plus conjugated forms of salicylic acid (total SA) in leaves of Les22 do not seem to differ significantly from those found in wild-type sibs (FIG. 2). Levels of free SA are slightly higher in Les22 leaf tissue compared to equivalent tissue of wild-type plants. However, it is not clear if this difference is sufficient to account for the enhanced resistance of Les22 against *C. heterostrophus*.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated protein comprising the amino acid sequence set forth in SEQ ID NO:2.

2. The protein of claim 1 that has the amino acid sequence set forth in SEQ ID NO:2.

3. An isolated protein that is at least 85% identical to the amino acid sequence set forth in SEQ ID NO:2, wherein said protein catalyzes the sequential decarboxylation of uroporphyrinogen III to coproporphyrinogen III.

4. The protein of claim 3 that is at least 90% identical to the amino acid sequence set forth in SEQ ID NO:2.

5. The protein of claim 3 that is at least 95% identical to the amino acid sequence set forth in SEQ ID NO:2.

6. An isolated protein of claim 3 comprising at least 100 contiguous amino acid residues of the amino acid sequence set forth in SEQ ID NO:2.

* * * * *

UNITED STATES PATENT AND TRADEMARK OFFICE
CERTIFICATE OF CORRECTION

PATENT NO.     : 6,455,297 B1
DATED          : September 24, 2002
INVENTOR(S)    : Johal et al.

It is certified that error appears in the above-identified patent and that said Letters Patent is hereby corrected as shown below:

<u>Title page,</u>
Item [75], Inventors:,
In the first inventor's address, "Johnston, IA" should read -- W, Lafayette, IN --.
In the fourth inventor's address, "Albany, CA" should read -- Hercules, CA --.

Item [73], Assignee:, insert -- The Curators of the University of Missouri, Columbia, MO --.

Signed and Sealed this

Eighth Day of April, 2003

JAMES E. ROGAN
*Director of the United States Patent and Trademark Office*

SEQUENCE LISTING

<160> NUMBER OF SEQ ID NOS: 5

<210> SEQ ID NO 1
<211> LENGTH: 1604
<212> TYPE: DNA
<213> ORGANISM: Zea mays
<220> FEATURE:
<221> NAME/KEY: CDS
<222> LOCATION: (137)..(1318)

<400> SEQUENCE: 1

```
ccccttccgat tctccgtcgc ctgagcggct gagccaacct tgccaagccca agcaagccaa      60 gtcgtcgcct ccccgaccca acgccgcgac ccccttgccc gtccgcgacc gctgcagcac     120
ctcggatccc gcccca atg gca aca gcg tgt ccg ccg ctc tcg ctg ccg tcc     172
               Met Ala Thr Ala Cys Pro Pro Leu Ser Leu Pro Ser
                 1               5                  10 acc tcc ctc ttc cgc ggc agg tcc gcc cgc gcc ggg ccc aac gca ggc       220
Thr Ser Leu Phe Arg Gly Arg Ser Ala Arg Ala Gly Pro Asn Ala Gly
             15                  20                  25 agc tca cgg ccg tcc gct gca gcg ccg tcg gag agg cgg tcg tgg agg       268
Ser Ser Arg Pro Ser Ala Ala Ala Pro Ser Glu Arg Arg Ser Trp Arg
         30                  35                  40 agg cct cgc cca gac ggc gga aga gcc gct gct ggt gag cgc aat cag       316
Arg Pro Arg Pro Asp Gly Gly Arg Ala Ala Ala Gly Glu Arg Asn Gln
     45                  50                  55                  60 agg gag gaa gtc gag agg cca ccc gtc tgg ctc atg agg cag gcc ggg       364
Arg Glu Glu Val Glu Arg Pro Pro Val Trp Leu Met Arg Gln Ala Gly
                 65                  70                  75 agg tac atg aag agc tac caa ttg ctc tgc gag cgg tat cct tcg ttc       412
Arg Tyr Met Lys Ser Tyr Gln Leu Leu Cys Glu Arg Tyr Pro Ser Phe
             80                  85                  90 cgt gaa aga tca gaa aat gtc gac cta gtt gtt gag atc tct ttg caa       460
Arg Glu Arg Ser Glu Asn Val Asp Leu Val Val Glu Ile Ser Leu Gln
             95                 100                 105 cca tgg aag gtt ttc aag cct gat gga gtc atc ttg ttc tcg gac atc       508
Pro Trp Lys Val Phe Lys Pro Asp Gly Val Ile Leu Phe Ser Asp Ile
         110                 115                 120 ctt act cca ctt cct ggg atg aac ata cct ttt gac att gtg aag gga       556
Leu Thr Pro Leu Pro Gly Met Asn Ile Pro Phe Asp Ile Val Lys Gly
125                 130                 135                 140 aaa ggt cca gtg atc tat gat cca ttg aga acg gca gca gct gtg aat       604
Lys Gly Pro Val Ile Tyr Asp Pro Leu Arg Thr Ala Ala Ala Val Asn
                 145                 150                 155 gaa gtc aga gaa ttt gtt cct gag gag tgg gtc cct tat gtg ggg cag       652
Glu Val Arg Glu Phe Val Pro Glu Glu Trp Val Pro Tyr Val Gly Gln
             160                 165                 170 gct ctg aat att ttg aga caa gag gtt aaa aat gaa gct gct gta cta       700
Ala Leu Asn Ile Leu Arg Gln Glu Val Lys Asn Glu Ala Ala Val Leu
         175                 180                 185 ggt ttt gtt gga gct ccg ttt acc ttg gca tct tat tgt gtg gaa gga       748
Gly Phe Val Gly Ala Pro Phe Thr Leu Ala Ser Tyr Cys Val Glu Gly
     190                 195                 200 ggt tca tca aag aac ttt aca ttg att aag aaa atg gcc ttc tca gaa       796
Gly Ser Ser Lys Asn Phe Thr Leu Ile Lys Lys Met Ala Phe Ser Glu
205                 210                 215                 220 cca gcg att tta cac aat ttg cta cag aag ttc aca aca tca atg gct       844
Pro Ala Ile Leu His Asn Leu Leu Gln Lys Phe Thr Thr Ser Met Ala
                 225                 230                 235 aac tat att aaa tac caa gcg gac aat ggg gcg cag gct gtc caa att       892
Asn Tyr Ile Lys Tyr Gln Ala Asp Asn Gly Ala Gln Ala Val Gln Ile
             240                 245                 250 ttc gat tca tgg gct act gaa ctc agc ccg gct gat ttt gag gag ttt       940
Phe Asp Ser Trp Ala Thr Glu Leu Ser Pro Ala Asp Phe Glu Glu Phe
         255                 260                 265 agc ctg cct tat cta aag cag ata gtg gat agt gtt agg gaa aca cat       988
Ser Leu Pro Tyr Leu Lys Gln Ile Val Asp Ser Val Arg Glu Thr His
     270                 275                 280 cct gac ttg cct ctg ata ctt tac gca agt gga tct ggg ggc ttg ctg      1036
Pro Asp Leu Pro Leu Ile Leu Tyr Ala Ser Gly Ser Gly Gly Leu Leu
```

```
                  285                 290                 295                 300
gag agg ctt cct ttg aca ggt gtt gat gtt gtc agc ttg gac tgg acg          1084
Glu Arg Leu Pro Leu Thr Gly Val Asp Val Val Ser Leu Asp Trp Thr
                305                 310                 315 gtc gat atg gca gag ggc agg aaa aga ttg gga tct aac aca gca gtc          1132
Val Asp Met Ala Glu Gly Arg Lys Arg Leu Gly Ser Asn Thr Ala Val
            320                 325                 330 caa ggg aac gtg gac cct ggt gtt ctt ttt gga tcc aaa gag ttt ata          1180
Gln Gly Asn Val Asp Pro Gly Val Leu Phe Gly Ser Lys Glu Phe Ile
            335                 340                 345 acg agg cgg att tac gac act gtg cag aag gct ggc aat gtt gga cat          1228
Thr Arg Arg Ile Tyr Asp Thr Val Gln Lys Ala Gly Asn Val Gly His
        350                 355                 360 gta ttg aac ctt ggc cat ggc atc aag gtt gga act ccg gag gaa aat          1276
Val Leu Asn Leu Gly His Gly Ile Lys Val Gly Thr Pro Glu Glu Asn
365                 370                 375                 380 gtt gct cac ttt ttt gag gtc gca aaa ggg atc aga tat taa                  1318
Val Ala His Phe Phe Glu Val Ala Lys Gly Ile Arg Tyr
                385                 390 agaacctggc atggttttt cctttttcca aatcggcaga agttgtagag tcggcggtcg         1378
aggatagatg cagaaagccc atgtgcagta tagagtgcct gaaaaaattt ttgggactga        1438
ttttgtttgt tgcatttcaa gttccggttt cagtgtaata ttgtaagcag atttgagtgg       1498
aggcgtaatg aagtgcctaa ttgtttatag caatatagtt ttgtacaacc agtatccttg        1558
tttatgagag tacgaagcag aaatactgat catgtgttga cagata                       1604

<210> SEQ ID NO 2
<211> LENGTH: 393
<212> TYPE: PRT
<213> ORGANISM: Zea mays

<400> SEQUENCE: 2

Met Ala Thr Ala Cys Pro Pro Leu Ser Leu Pro Ser Thr Ser Leu Phe
  1               5                  10                  15

Arg Gly Arg Ser Ala Arg Ala Gly Pro Asn Ala Gly Ser Ser Arg Pro
             20                  25                  30

Ser Ala Ala Ala Pro Ser Glu Arg Arg Ser Trp Arg Arg Pro Arg Pro
         35                  40                  45

Asp Gly Gly Arg Ala Ala Ala Gly Glu Arg Asn Gln Arg Glu Glu Val
     50                  55                  60

Glu Arg Pro Pro Val Trp Leu Met Arg Gln Ala Gly Arg Tyr Met Lys
 65                  70                  75                  80

Ser Tyr Gln Leu Leu Cys Glu Arg Tyr Pro Ser Phe Arg Glu Arg Ser
                 85                  90                  95

Glu Asn Val Asp Leu Val Val Glu Ile Ser Leu Gln Pro Trp Lys Val
            100                 105                 110

Phe Lys Pro Asp Gly Val Ile Leu Phe Ser Asp Ile Leu Thr Pro Leu
        115                 120                 125

Pro Gly Met Asn Ile Pro Phe Asp Ile Val Lys Gly Lys Gly Pro Val
    130                 135                 140

Ile Tyr Asp Pro Leu Arg Thr Ala Ala Val Asn Glu Val Arg Glu
145                 150                 155                 160

Phe Val Pro Glu Glu Trp Val Pro Tyr Val Gly Gln Ala Leu Asn Ile
                165                 170                 175

Leu Arg Gln Glu Val Lys Asn Glu Ala Ala Val Leu Gly Phe Val Gly
            180                 185                 190
```

```
Ala Pro Phe Thr Leu Ala Ser Tyr Cys Val Glu Gly Gly Ser Ser Lys
        195                 200                 205
Asn Phe Thr Leu Ile Lys Lys Met Ala Phe Ser Glu Pro Ala Ile Leu
        210                 215                 220
His Asn Leu Leu Gln Lys Phe Thr Thr Ser Met Ala Asn Tyr Ile Lys
225                 230                 235                 240
Tyr Gln Ala Asp Asn Gly Ala Gln Ala Val Gln Ile Phe Asp Ser Trp
                245                 250                 255
Ala Thr Glu Leu Ser Pro Ala Asp Phe Glu Phe Ser Leu Pro Tyr
            260                 265                 270
Leu Lys Gln Ile Val Asp Ser Val Arg Glu Thr His Pro Asp Leu Pro
            275                 280                 285
Leu Ile Leu Tyr Ala Ser Gly Ser Gly Gly Leu Leu Glu Arg Leu Pro
290                 295                 300
Leu Thr Gly Val Asp Val Val Ser Leu Asp Trp Thr Val Asp Met Ala
305                 310                 315                 320
Glu Gly Arg Lys Arg Leu Gly Ser Asn Thr Ala Val Gln Gly Asn Val
                325                 330                 335
Asp Pro Gly Val Leu Phe Gly Ser Lys Glu Phe Ile Thr Arg Arg Ile
            340                 345                 350
Tyr Asp Thr Val Gln Lys Ala Gly Asn Val Gly His Val Leu Asn Leu
        355                 360                 365
Gly His Gly Ile Lys Val Gly Thr Pro Glu Glu Asn Val Ala His Phe
    370                 375                 380
Phe Glu Val Ala Lys Gly Ile Arg Tyr
385                 390

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 3
cgccaacgcc tccatttcgt cgaatcc                                      27

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 4
cttgccttca tgtacctccc g                                            21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:Synthetic
      Oligonucleotide

<400> SEQUENCE: 5
cgggaggtac atgaaggcaa g                                            21
```